United States Patent [19]

Horn

[11] Patent Number: 5,023,285

[45] Date of Patent: Jun. 11, 1991

[54] BIS (TRI-TERTIARY-ALKYLPHENOXY) DIPHOSPHASPIROUNDECANES

[75] Inventor: William E. Horn, Gibsonia, Pa.

[73] Assignee: G E Specialty Chemicals, Parkersburg, W. Va.

[21] Appl. No.: 223,318

[22] Filed: Jul. 25, 1988

[51] Int. Cl.$^5$ ............................. C08K 5/54; C07F 9/15
[52] U.S. Cl. ..................................... 524/120; 558/78; 252/400.24
[58] Field of Search ................... 252/400.24; 524/120; 558/78

[56] References Cited

U.S. PATENT DOCUMENTS

| | | | |
|---|---|---|---|
| 3,201,437 | 8/1965 | Lester et al. | 524/120 |
| 4,066,611 | 1/1978 | Axelrod | 524/120 |
| 4,094,855 | 6/1978 | Spivack | 524/120 |
| 4,207,229 | 6/1980 | Spivack | 524/120 |
| 4,290,976 | 9/1981 | Hechenbleikner et al. | 558/78 |
| 4,305,866 | 12/1981 | York et al. | 558/78 |
| 4,312,818 | 1/1982 | Maul et al. | 558/95 |
| 4,520,149 | 5/1985 | Golder | 524/120 |
| 4,585,818 | 4/1986 | Jung et al. | 524/120 |
| 4,692,539 | 9/1987 | Spivack | 558/78 |
| 4,739,090 | 4/1988 | Tajima et al. | 558/78 |

FOREIGN PATENT DOCUMENTS

| | | |
|---|---|---|
| 038876 | 11/1981 | European Pat. Off. . |
| 199997 | 11/1986 | European Pat. Off. . |
| 49-128044 | 12/1974 | Japan . |
| 62-167338 | 7/1987 | Japan . |
| 2156358 | 10/1985 | United Kingdom . |

OTHER PUBLICATIONS

Patent Abstract of Japan, vol. 3, No. 50 of Japanese Reference No. 54–25951 dated Feb. 27, 1979.
Patent Abstracts of Japan, vol. 5, No. 194, dated Dec. 10, 1981, of Japanese Reference No. 56–113790 dated Sep. 7, 1981.

*Primary Examiner*—Kriellion Morgan
*Attorney, Agent, or Firm*—Lowe, Price, LeBlanc, Becker & Shur

[57] ABSTRACT

A composition is provided which comprises a 3,9-bis (2,4,6-tri-t-alkylphenoxy)-2,4,8,10-tetroxa-3,9-diphosphaspiro[5.5]undecane, and polymer compositions are provided which include a polymer and an effective amount of one or more 3,9-bis(2,4,6-tri-t-alkylphenoxy)-2,4,8,10-tetroxa-3,9-diphosphaspiro[5.5]undecane.

10 Claims, No Drawings

BIS (TRI-TERTIARY-ALKYLPHENOXY) DIPHOSPHASPIROUNDECANES

BACKGROUND OF THE INVENTION

The present invention relates to bis (tri-tert-alkylphenoxy) diphosphaspiroundecanes, and to bis (2,4,6-tri-t-alkylphenoxy) diphosphaspiroundecanes in particular, as well as to polymer compositions which include tri-t-alkylphenoxy diphosphaspiroundecanes in stabilizing amounts.

A variety of alkylphenoxy diphosphaspiroundecanes are known in the art. Japanese Early Disclosure 1986-225, 191 of Oct. 9, 1986 by Tajima et al. discloses a number of bis (alkylphenoxy) diphosphaspiroundecanes, such as, bis(2-tert-butyl-4,6-dimethylphenoxy) diphosphaspiroundecane and bis(2,4-di-t-octylphenoxy) diphosphaspiroundecane. Bis (alkylphenoxy) diphosphaspiroundecanes are also disclosed by Japanese Patent No. 49-128044; U.S. Pat. Nos. 4,066,611 to Axelrod; 4,094,855 and 4,207,229 to Spivack; 4,305,866 to York et al.; 4,520,149 to Golder; 4,585,818 to Jung et al.; U.K. Patent Application GB No. 2 156 358 A and Japanese Patent Application 52 [1977]110829, Sept. 14, 1977, to Risner et al. Other diphosphaspiroundecane compounds known in the art include bis (2,6-di-t-butyl-4-methylphenoxy) diphosphaspiroundecane and bis (2,6-di-t-butyl-4-ethylphenoxy) diphosphaspiroundecane.

Virtually all commercial polymers contain one or more stabilizing compounds to protect the polymer against degradation of polymer properties by chain scission or undesired crosslinking during processing and product use. This degradation is particularly problematical with thermoplastic polymers, which typically are subjected to extreme processing temperatures. Not only does such degradation effect the physical properties of the composition, but may also cause the polymer to become discolored, thereby making the polymer aesthetically unappealing and causing the product to be rejected.

However, polymer stabilizers may be exposed to various adverse conditions during the course of their production, shipment, storage and use. One such condition which may adversely affect stabilizers is excessive to moisture either in the form of humidity or wetness. Although many stabilizers are used in the form of powders or granules, absorption of moisture may cause a stabilizer to clump or "block" thereby making the stabilizer difficult to handle during feeding and mixing operations. A consequence of such moisture exposure may be hydrolysis, which frequently reduces stabilizing properties and leaves the resin vulnerable to degradation.

Many phosphites, including some of the above-mentioned diphosphaspiroundecanes, may provide excellent stabilization when properly stored, either neat or after being compounded into the polymer. A few phosphites, such as tris(2,4-di-t-butylphenol)phosphite (TBPP), may exhibit good storage stability in humid environments, but do not provide the stabilizing efficacy of many members of the diphosphaspiroundecane class of stabilizer.

Although many of the above diphosphaspiroundecanes are capable of acting as polymer stabilizers, an improvement in the overall balance of properties would be realized if moisture resistance could be improved while maintaining excellent stabilizing properties. Indeed, a stabilizer which imparts good physical and color stability to a polymer while exhibiting improved resistance to moisture and hydrolysis offers significant practical advantages over many stabilizers known in the art.

SUMMARY OF THE INVENTION

The present invention is a composition which comprises a diphosphaspiroundecane of the general formula:

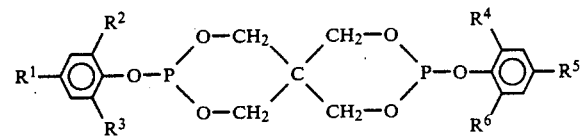

wherein each of $R^1$, $R^2$, $R^3$, $R^4$, $R^5$ and $R^6$ is a tertiary alkyl moiety. In the embodiment which is preferred $R^1$, $R^2$, $R^3$, $R^4$, $R^5$ and $R^6$ are selected from the group consisting of $C_4$ to about $C_{12}$ tertiary alkyl moieties. Tertiary-butyl is the moiety which is most preferred.

The present invention also is directed to a stabilized polymer composition which comprises a polymer and an effective amount of the diphosphaspiroundecane of the invention. Thermoplastic polymers are preferred, with polyethylene, polypropylene, polyethylene terephthalate, polyphenylene ether, polystyrene, impact polystyrene and ABS-type graft copolymers being most preferred.

DETAILED DESCRIPTION OF THE INVENTION

The present invention comprises a 3,9-bis(2,4,6-tri-t-alkylphenoxy)-2,4,8,10-tetroxa-3,9-diphosphaspiro[5.5]undecane. These compounds, also known as bis (2,4,6-tri-t-alkylphenyl) pentaerythritol diphosphites, may be represented by the general formula:

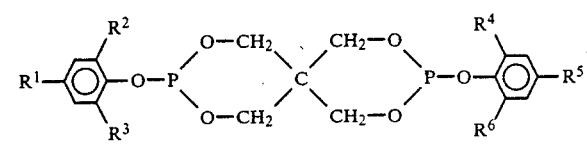

wherein each of $R^1$, $R^2$, $R^3$, $R^4$, $R^5$ and $R^6$ are tertiary (or "tert" or "t") alkyl moieties.

Examples of such moieties include t-butyl, t-pentyl, 1,1,4,4-tertramethyl butyl, t-octyl, 1-methyl cyclohexyl, t-dodecyl and 2-phenyl-2-propyl. However, $C_4$ to about $C_{12}$ moieties, such as t-butyl, t-pentyl, t-octyl and t-dodecyl are preferred. Relatively smaller groups, such as t-butyl, t-pentyl, 1-methylcyclohexyl and 1,1,4,4-tetramethyl butyl are more preferred. Tertiary butyl moieties are most preferred. Although any or all of $R^1$, $R^2$, $R^3$, $R^4$, $R^5$ and $R^6$ may be selected to be different, such as in 2,4-di-t-butyl-4-t-pentyl, it is preferred that $R^1$, $R^2$, $R^3$, $R^4$, $R^5$ and $R^6$ be the same.

The diphosphaspiroundecanes of the present invention may be made by means known in the art, such as by the reaction of a tri-t-alkylphenol with 3,9-dichloro-2,4,8,10-tetroxa-3,9-diphosphaspiro[5.5]undecane (which may be formed by the reaction of pentaerythritol with phosphorous trichloride by means known in the art). For example, 3,9-bis(2,4,6-tri-t-butylphenoxy)-2,4,8,10-tetroxa-3,9-diphosphaspiro[5.5]undecane may be formed by the reaction of 2,4,6-tri-t-butylphenol with 3,9-dichloro-2,4,8,10-tetroxa-3,9-diphosphaspiro[5.5]undecane (dichloropentite). Similarly, 3,9-bis(2,4,6-tri-t-pentyl phenoxy)-2,4,8,10-tetroxa-3,9-diphosphaspiro [5.5] undecane may be formed by the reaction of 2,4,6-tri-t-pentyl phenol with dichloropentite. Other bis(tri-t-alkylphenoxy)-tetroxa-diphosphaspiroundecanes may be formed by reacting the tri-t-alkylphenol corresponding to the desired tri-t-alkylphenoxy group with dichloropentite.

The diphosphaspiroundecanes of the present invnetion may also be made by reacting a phenol corresponding to the desired tri-t-alkylphenoxy group with phosphorous trichloride to form a tri-t-alkylphenoxy phosphorodichloridite, followed by reaction of the phosphorodichloridite with pentaerythritol to form a bis (tri-t-alkylphenoxy)-tetroxa-diphosphaspiroundecane. For example 2,4,6-tri-t-butylphenol may be reacted with phosphorous trichloride and then with pentaerythritol to form bis(2,4,6-tri-t-butyl-phenoxy)-tetroxa-diphosphaspiroundecane. Similarly, 2,4,6-tri-t-dodecyl-phenol might be reacted with phosphorous trichloride and then with pentaerythritol to form bis(2,4,6-tri-t-docecylphenoxy)-tetroxa-diphosphaspiroundecane.

Procedures for forming diphosphaspiroundecanes by the dichloropentite and the phosphorodichoridite routes are known in the art. However, whereas the prior art may show the diphosphaspiroundecane being formed in solution in the presence of an amine, such as triethylamine, which serves as an acid acceptor by forming an insoluble hydrochloride salt, it is preferred that the diphosphaspiroundecane be formed in a tri-n-alkylamine, such as tri-n-butylamine, wherein each n-alkyl group is a $C_3$ or larger n-alkyl moiety, wherein the hydrochloride salt remains in solution and the diphosphaspiroundecane product is substantially insoluble. Preferred processes are explained further in co-pending application U.S. Ser. No. 07/233,319, filed simultaneously with the present application, entitled "3,9-Diphosphaspiroundecanes and Process for Making 3,9-Diphosphaspiroundecanes", by S. J. Hobbs, K. J. Sheehan and W. P. Enlow, the disclosure of which is incorporated herein by reference. Examples of both prior art and preferred processes for making diphosphaspiroundecanes of the invention are shown below in the section entitled "Specific Embodiments".

The present invention also is a stabilized polymer composition which includes an effective amount of one or more of the bis (tri-t-alkylphenoxy)-tetroxa-diphosphaspiroundecanes described above. An amount of the diphosphaspiroundecanes of the invention is considered to be an "effective amount", when the polymer composition containing the diphosphaspiroundecane of the invention shows improved stability in any of its physical or color properties in comparison to an analogous polymer composition which does not include a diphosphaspiroundecane of the invention. In most polymer compositions, however, it will be preferred that the diphosphaspiroundecane of the invention be present in an amount equal to about 0.01 to about 2 parts by weight per 100 parts by weight resin (phr). Amounts of about 0.01 to about 1 phr are more preferred, although most compositions will contain about 0.025 phr or more.

The polymer may be any of the polymers known in the art, such as polyesters, polyurethanes, polyalkylene terephthalates, polysulfones, polyimides, polyphenylene ethers, styrenic polymers, poly carbonates, acrylic polymers, polyamides, polyacetals, halide containing polymers and polyolefin homopolymers and copolymers. Mixtures of different polymers, such as polyphenylene ether/styrenic resin blends, polyvinylchloride/ABS or other impact modified polymers, such as methacrylonitrile containing ABS, and polyester-/ABS or polyester plus some other impact modifier may also be used. Such polymers are available commercially or may be made by means well known in the art. However the diphosphaspiroundecanes of the invention are particularly useful in thermoplastic polymers, such as polyolefins, polycarbonates, polyesters, polyphenylene ethers and styrenic polymers, due to the extreme temperatures at which thermoplastic polymers are often processed and/or used.

Polymers of monoolefins and diolefins, for example polypropylene, polyisobutylene, polybutene-1, polymethylpentene-1, polyisoprene or polybutadiene, as well as polymers of cycloolefins, for instance of cyclopentene or norbornene, polyethylene (which optionally can be crosslinked), for example high density polyethylene (HDPE), low density polyethylene (LDPE) and linear low density polyethylene (LLDPE) may be used. Mixtures of these polymers, for example mixtures of polypropylene with (PP) polyisobutylene, polypropylene with polyethylene (for example PP/HDPE, PP/LDPE) and mixtures of different types of polyethylene (for example LDPE/HDPE), may also be used. Also useful are copolymers of monoolefins and diolefines with each other or with other vinyl monomers, such as, for example, ethylene/propylene, LLDPE and its mixtures with LDPE, propylene/butene-1, ethylene/hexene, ethylene/ethylpentene, ethylene/heptene, ethylene/octene, propylene/isobutylene, ethylene/butane-1, propylene/butadiene, isobutylene/isoprene, ethylene/alkyl acrylates, ethylene/alkyl methacrylates, ethylene/vinyl acetate (EVA) or ethylene/acrylic acid copolymers (EAA) and their salts (ionomers) and terpolymers of ethylene with propylene and a diene, such as hexadiene, dicyclopentadiene or ethylidene-norbornene; as well as mixtures of such copolymers and their mixtures with polymers mentioned above, for example polypropylene/ethylene-propylene-copolymers, LDPE/EVA, LDPE/EAA, LLDPE/EVA and LLDPE/EAA.

Thermoplastic polymers may also include styrenic polymers, such as polystyrene, poly-(p-methylstyrene), poly-(alpha-methylstyrene), copolymers of styrene or alpha-methylstyrene with dienes or acrylic derivatives, such as, for example, styrene/butadiene, styrene/acrylonitrile, styrene/alkyl methacrylate, styrene/maleic anhydride, styrene/butadiene/ethyl acrylate/-styrene/acrylonitrile/methylacrylate; mixtures of high impact strength from styrene copolymers and another polymer, such as, for example, from a polyacrylate, a diene polymer or an ethylene/propylene/diene terpolymer; and block copolymers of styrene, such as, for example, styrene/butadiene/styrene, styrene/isoprene/styrene, styrene/ethylene/butylene/styrene or styrene/ethylene/propylene/styrene. Styrenic polymers may additionally or alternatively include graft copolymers of styrene or alpha-methylstyrene such as, for example, styrene on polybutadiene, styrene on polybutadiene-styrene or polybutadiene-acrylonitrile; styrene and acrylonitrile (or methacrylonitrile) on polybutadiene; styrene and maleic anhydride or maleimide on polybutadiene; styrene, acrylonitrile and maleic anhydride or maleimide on polybutadiene; styrene, acrylonitrile and methyl methacrylate on polybutadiene, styrene and alkyl acrylates or methacrylates on polybutadiene, styrene and acrylonitrile on ethylene/propylene/diene terpolymers, styrene and acrylonitrile on polyacrylates or polymethacrylates, styrene and acrylonitrile on acrylate/butadiene copolymers, as well as mixtures of with the styrenic copolymers indicated above.

Nitrile polymers are also useful in the polymer composition of the invention. These include homopolymers and copolymers of acrylonitrile and its analogs such as methacrylonitrile, such as polyacrylonitrile, acrylonitrile/butadiene polymers, acrylonitrile/alkyl acrylate polymers, acrylonitrile/alkyl methacrylate/butadiene polymers, ABS, and ABS which includes methacrylonitrile.

Polymers based on acrylic acids, such as acrylic acid, methacrylic acid, methyl methacrylic acid and ethacrylic acid and esters thereof may also be used. Such polymers include polymethylmethacrylate, and ABS-type graft copolymers wherein all or part of the acrylonitrile-type monomer has been replaced by an acrylic acid ester or an acrylic acid amide. Polymers including other acrylic-type monomers, such as acrolein, methacrolein, acrylamide and methacrylamide may also be used.

Halogen-containing polymers may also be useful. These include resins such as polychloroprene, epichlorohydrin homo-and copolymers, polyvinyl chloride, polyvinyl bromide, polyvinyl fluoride, polyvinylidene chloride, chlorinated polyethylene, chlorinated polypropylene, florinated polyvinylidene, brominated polyethylene, chlorinated rubber, vinyl chloride-vinylacetate copolymer, vinyl chloride-ethylene copolymer, vinyl chloride-propylene copolymer, vinyl chloride-styrene copolymer, vinyl chloride-isobutylene copolymer, vinyl chloride-vinylidene chloride copolymer, vinyl chloride-styrene-maleic anhydride tercopolymer, vinyl chloride-styrene-acrylonitrile copolymer, vinyl chloride-butadiene copolymer, vinyl chloride-isoprene copolymer, vinyl chloride-chlorinated propylene copolymer, vinyl chloride-vinylidene chloride-vinyl acetate tercopolymer, vinyl chloride-acrylic acid ester copolymers, vinyl chloride-maleic acid ester copolymers, vinyl chloride-methacrylic acid ester copolymers, vinyl chloride-acrylonitrile copolymer and internally plasticized polyvinyl chloride.

Other useful thermoplastic polymers include homopolymers and copolymers of cyclic ethers, such as polyalkylene glycols, polyethylene oxide, polypropylene oxide or copolymers thereof with bis-glycidyl ethers; polyacetals, such as polyoxymethylene and those polyoxymethylene which contain ethylene oxide as a comonomer; polyacetals modified with thermoplastic polyurethanes, acrylates or methacrylonitrile containing ABS; polyphenylene oxides and sulfides, and mixtures of polyphenylene oxides with polystyrene or polyamides; polycarbonates and polyester-carbonates; polysulfones, polyethersulfones and polyetherketones; and polyesters which are derived from dicarboxylic acids and diols and/or from hydroxycarboxylic acids or the corresponding lactones, such as polyethylene terephthalate, polybutylene terephthalate, poly-1,4-dimethylol-cyclohexane terephthalate, poly-[2,2-4(4-hydroxyphenyl)-propane] terephthalate and polyhydroxybenzoates as well as block-copolyetheresters derived from polyethers having hydroxyl end groups.

Polyamides and copolyamides which are derived from diamines and dicarboxylic acids and/or from aminocarboxylic acids or the corresponding lactams, such as polyamide, 4, polyamide 6, polyamide 6/6, 6/10, 6/9, 6/12 and 4/6, polyamide 11, polyamide 12, aromatic polyamides obtained by condensation of m-xylene, diamine and adipic acid; polyamides prepared from hexamethylene diamine and isophthalic or/and terephthalic acid and optionally an elastomer as modifier, for example poly-2,4,4-trimethylhexamethylene terephthalamide or poly-m-phenylene isophthalamide may be useful. Further copolymers of the aforementioned polyamides with polyolefins, olefin copolymers, ionomers or chemically bonded or grafted elastomers; or with polyethers, such as for instance, with polyethylene glycol, polypropylene glycol or polytetramethylene glycols, and polyamides or copolyamides modified with EPDM or ABS may be used.

Polyolefin, polyalkylene terephthalate, polyphenylene ether and styrenic resins, and mixtures thereof are more preferred, with polyethylene, polypropylene, polyethylene terephthalate, polyphenylene ether homopolymers and copolymers, polystyrene, high impact polystyrene, polycarbonates and ABS-type graft copolymers and mixtures thereof being particularly preferred.

The resulting stabilized polymer compositions of the invention may optionally also contain various conventional additives, such as the following.

1. Antioxidants 1.1 Alkylated monophenols, for example: 2,6-di-tert-butyl-4-methylphenol, 2-tert-butyl-4,6-dimethylphenol, 2,6-di-tert-butyl-4-ethylphenol, 2,6-di-tert-butyl-4-n-butylphenol, 2,6-di-tert-butyl-4-i-butylphenol, 2,6-dicyclopentyl-4-methylphenol, 2-(alpha-methylcyclohexyl)-4,6-dimethylphenol, 2,6-di-octadecyl-4-methylphenol, 2,4,6-tri-cyclohexylphenol, 2,6-di-tert-butyl-4-methoxymethylphenol.

1.2 Alkylated hydroquinones for example, 2,6-di-tert-butyl-4-methoxyphenol, 2,5-di-tert-butyl-hydroquinone, 2,5-di-tert-amyl-hydroquinone, 2,6-diphenyl-4-octadecyloxyphenol.

1.3 Hydroxylated thiodiphenyl ethers, for example, 2,2'-thio-bis-(6-tert-butyl-4-methylphenol), 2,2'-thio-bis-(4-octylphenol), 4,4'-thio-bis-(6-tert-butyl-3-methylphenol), 4,4'-thio-bis-(6-tert-butyl-2-methylphenol).

1.4 Alkyliden-bisphenols, for example, 2,2'-methylene-bis-(6-tert-butyl-4-methylphenol), 2,2'-methylene-bis-(6-tert-butyl-4-ethylphenol), 2,2'-methylene-bis-[4-methyl-6-(alpha-methylcyclohexyl)phenol], 2,2'-methylene-bis-(4-methyl-6-cyclohexylphenol), 2,2'-methylene-bis-(6-nonyl-4-methylphenol), 2,2'-methylene-bis-[6-(alpha-methylbenzyl)-4-nonylphenol], 2,2'-methylene-bis-[6-(alpha,alpha-dimethylbenzyl)-4-nonylphenol], 2,2'-methylene-bis-(4,6-di-tert-butylphenol), 2,2'-ethylidene-bis-(4,6-di-tert-butylphenol), 2,2'-ethylidene-bis-(6-tert-butyl-4-isobutylphenol), 4,4'-methylene-bis-(2,6-di-tert-butylphenol), 4,4'-methylene-bis-(6-tert-butyl-2-methylphenol), 1,1-bis-(5-tert-butyl-4-hydroxy-2-methylphenyl)butane, 2,6-di-(3-tert-butyl-5-methyl-2-hydroxybenzyl)-4-methylphenol, 1,1,3-tris-(5-tert-butyl-4-hydroxy-2-methylphenyl)butane, 1,1-bis-(5-tert-butyl-4-hydroxy-2-methylphenyl)-3-dodecylmercaptobutane, ethylenglycol-bis-[3,3-bis-(3'-tert-butyl-4'-hydroxy-phenyl)-butyrate], di-(3-tert-butyl-4-hydroxy-5-methylphenyl)-dicyclopentadiene, di-[2-(3'-tert-butyl-2'-hydroxy-5'-methyl-benzyl)-6-tert-butyl-4-methylphenyl]-terephthalate.

1.5 Benzyl compounds, for example, 1,3,5-tris-(3,5-di-tert-butyl-4-hydroxybenzyl)-2,4,6-trimethylbenzene, bis-(3,5-di-tert-butyl-4-hydroxybenzyl)sulfide, isooctyl 3,5-di-tert-butyl-4-hydroxybenzyl-mercapto-acetate, bis-(4-tert-butyl-3-hydroxy-2,6-dimethylbenzyl)dithiolterephthalate, 1,3,5-tris-(3,5-di-tert-butyl-4-hydroxybenzyl)isocyanurate, 1,3,5-tris-(4-tert-butyl-3-hydroxy-2,6-dimethylbenzyl)isocyanurate, dioctadecyl 3,5-di-tert-butyl-4-hydroxybenzyl-phosphonate, calcium salt of monoethyl 3,5-di-tert-butyl-4-hydroxybenzylphosphonate, 1,3,5-tris(3,5-dicyclohexyl-4-hydroxybenzyl)isocyanurate.

1.6 Acylaminophenols, for example, 4-hydroxy-lauric acid anilide, 4-hydroxy-stearic acid anilide, 2,4-bis-octylmercapto-6-(3,5-tert-butyl-4-hydrox-yanilino)-s-triazine, octyl-N-(3,5-di-tert-butyl-4-hydroxyphenyl)-carbamate.

1.7 Esters of beta-(3,5-di-tert-butyl-4-hydroxyphenyl)-propionic acid with monohydric or polyhydric alcohols, for example, methanol, diethyleneglycol, octadecanol, triethyleneglycol, 1,6-hexanediol, pentaerythritol, neopentylglycol, tris-hydroxyethyl isocyanurate, thiodiethyleneglycol, dihydroxyethyl oxalic acid diamide.

1.8 Esters of beta-(5-tert-butyl-4-hydroxyl-3-methylphenyl)-propionic acid with monohydric or polyhydric alcohols, for example, methanol, diethyleneglycol, octadecanol, triethyleneglycol, 1,6-hexanediol, pentaerythritol, neopentylglycol, tris-hydroxyethyl isocyanurate, thiodiethyleneglycol, dihydroxyethyl oxalic acid diamide.

1.9 Esters of beta-(5-tert-butyl-4-hydroxy-3-methylphenyl)propionic acid with mono-or polyhydric alcohols, e.g. with methanol, diethylene glycol, octadecanol, triethylene glycol, 1,6-hexanediol, pentaerythritol, neopentyl glycol, tris(hydroxyethyl) isocyanurate, thiodiethylene glycol, N,N'-bis(hydroxyethyl)oxalic acid diamide.

1.10 Amides of beta-(3,5-di-tert-butyl-4-hydroxyphenyl)-propionic acid for example, N,N'-di-(3,5-di-tert-butyl-4-hydroxyphenylpropionyl)-hexamethylendiamine, N,N'-di-(3,5-di-tert-butyl-4-hydroxyphenylpropionyl)-trimethylendiamine, N,N'-di-(3,5-di-tert-butyl-4-hydroxyphenylpropionyl)-hydrazine.

2. UV absorbers and light stabilizers.

2.1 2-(2'-Hydroxyphenyl)-benzotriazoles, for example, the 5'methyl-, 3',5'-di-tert-butyl-, 5'-tert-butyl-, 5'-(1,1,3,3-tetramethylbutyl)-, 5-chloro-3',5'-di-tert-butyl-, 5-chloro-3'-tert-butyl-5'-methyl-, 3'-sec-butyl-5'-tert-butyl-, 4'-octoxy, 3',5'-di-tert-amyl-, 3',5'-bis-(alpha,alpha-dimethylbenzyl)-derivatives.

2.2 2-Hydroxy-benzophenones, for example, the 4-hydroxy-, 4-methoxy-, 4-octoxy, 4-decyloxy-, 4-dodecyloxy-, 4-benzyloxy, 4,2',4'-trihydroxy- and 2'-hydroxy-4,4'-dimethoxy derivative.

2.3 Ester of substituted and unsubstituted benzoic acids for example, phenyl salicylate, 4-tert-butyl-phenylsalicilate, octylphenyl salicylate, dibenzoylresorcinol, bis-(4-tert-butylbenzoyl)-resorcinol, benzoyl-resorcinol, 2,4-di-tert-butyl-phenyl-3,5-di-tert-butyl-4-hydroxybenzoate and hexadecyl-3,5-di-tert-butyl-4-hydroxybenzoate.

2.4 Acrylates, for example, alpha-cyano-beta,beta-diphenylacrylic acid ethyl ester or isooctyl ester, alpha-carbomethoxy-cinnamic acid methyl ester, alpha-cyano-beta-methyl-p-methoxy-cinnamic acid methyl ester or butyl ester, alpha-carbomethoxy-p-methoxy-cinnamic acid methyl ester, N-(beta-carbomethoxy-beta-cyano-vinyl)-2-methyl-indoline.

2.5 Nickel compounds, for example, nickel complexes of 2,2'-thio-bis-[4-(1,1,3,3-tetramethylbutyl)-phenol], such as the 1:1 or 1:2 complex, optionally with additional ligands such as n-butylamine, triethanolamine or N-cyclohexyl-di-ethanolamine, nickel dibutyldithiocarbamate, nickel salts of 4-hydroxy-3,5-di-tert-butylbenzylphosphonic acid monoalkyl esters, such as of the methyl, ethyl or butyl ester, nickel complexes of ketoximes such as of 2-hydroxy-4-methyl-penyl undecyl ketoxime, nickel complexes of 1-phenyl-4-lauroyl-5-hydroxy-pyrazol, optionally with additional ligands.

2.6 Sterically hindered amines, for example bis-(2,2,6,6-tetramethylpiperidyl)-sebacate, bis-(1,2,2,6,6-pentamethylpiperidyl)-sebacate, n-butyl-3,5-di-tert-butyl-4-hydroxybenzyl malonic acid bis-(1,2,2,6,6-pentamethylpiperidyl)ester, condensation product of 1-hydroxyethyl-2,2,6,6-tetramethyl-4-hydroxy-piperidine and succinic acid, condensation product of N,N'-(2,2,6,6-tetramethylpiperidyl)-hexamethylendiamine and 4-tert-octylamino-2,6-dichloro-1,3,5-s-triazine, tris-(2,2,6,6-tetramethylpiperidyl)-nitrilotriacetate, tetrakis-(2,2,6,6-tetramethyl-4-piperidyl)-1,2,3,4-butane-tetracarbonic acid, 1,1'(1,2-ethanediyl)-bis-(3,3,5,5-tetramethylpiperazinone). Such amines include hydroxylamines derived from hindered amines, such as di(1-hydroxy-2,2,6,6-tetramethylpiperidin-4-yl)sebacate; 1-hydroxy-2,2,6,6-tetramethyl-4-benzoxypiperidine; 1-hydroxy-2,2,6,6-tetramethyl-4-(3,5-di-tert-butyl-4-hydroxy hydrocinnamoyloxy)-piperidine; and N-(1-hydroxy-2,2,6,6-tetramethylpiperidin-4-yl)-epsilon-caprolactam.

2.7 Oxalic acid diamides, for example, 4,4'-di-octyloxy-oxanilide, 2,2'-di-octyloxy-5,5'-di-tert-butyloxanilide, 2,2'-di-dodecyloxy-5,5'-di-tert-butyl-oxanilide, 2-ethoxy-2'-ethyl-oxanilide, N,N'-bis(3-dimethylaminopropyl)-oxalamide, 2-ethoxy-5-tert-butyl-2'-ethyloxanilide and its mixture with 2-ethoxy-2'-ethyl-5,4'-di-tert-butyloxanilide and mixtures of ortho- and para-methoxy- as well as of o- and p-ethoxy-disubstituted oxanilides.

3. Metal deactivators, for example, N,N'-diphenyloxalic acid diamide, N-salicylal-N'-salicyloylhydrazine, N,N'-bis-salicyloylhydrazine, N,N'-bis-(3,5-di-tert-butyl-4-hydroxyphenylpropionyl)-hydrazine, salicyloylamino-1,2,4-triazole, bis-benzyliden-oxalic acid dihydrazide.

4. Phosphites and phosphonites, for example triphenyl phosphite, diphenylalkyl phosphites, phenyldialkyl phosphites, tris(nonyl-phenyl) phosphite, trilauryl phosphite, trioctadecyl phosphite, distearyl pentaerythritol diphosphite, tris(2,4-di-tert-butylphenyl)phosphite, diisodecyl pentaerythritol diphosphite, bis(2,4-di-tert-butylphenyl) pentaerythritol diphosphite, tristearyl sorbitol triphosphite, and tetrakis (2,4-di-tert-butylphenyl) 4,4'-biphenylene diphosphonite.

5. Peroxide scavengers, for example esters of beta-thiodipropionic acid, for example the lauryl stearyl, myristyl or tridecyl esters, mercaptobenzimidazole or the zinc salt of 2-mercaptobenzimidazole, zinc-dibutyldithiocaramate, dioctadecyldisulfide, pentaerythritoltetrakis(beta-dodecylmercapto)-propionate.

6. Polyamide stabilizers, for example copper salts in combination with iodides and/or phosphorus compounds and salts of divalent manganese.

7. Basic co-stabilizers, for example, melamine, polyvinylpyrrolidone, dicyandiamide, triallyl cyanurate, urea derivatives, hydrazine derivatives, amines, polyamides, polyurethanes, alkali metal salts and alkaline earth metal salts of higher fatty acids for example Ca stearate, Zn stearate, Mg stearate, Na ricinoleate and K palmitate, antimony pyrocatecholate or zinc pyrocatecholate.

8. Nucleating agents, for example, 4-tert-butyl-benzoic acid, adipic acid, diphenylacetic acid.

9. Fillers and reinforcing agents, for example, calcium carbonate, silicates, glass fibres, asbestos, talc, kaolin, mica, barium sulfate, metal oxides and hydroxides, carbon black, graphite.

10. The present invention may also be used in conjunction with aminoxy propanoate derivatives such as methyl-3-[N,N-dibenzylaminoxy]propanoate; ethyl-3-[N,N-dibenzylaminoxy]propanoate; 1,6-hexamethylene-bis[3-(N,N-dibenzylaminoxy)propanoate]; methyl-[2-(methyl)-3(N,N-dibenzylaminoxy)propanoate]; octadecyl-3-[N,N-dibenzyl-aminoxy]propanoic acid; tetrakis[(N,N-dibenzylaminoxy)ethyl carbonyl oxymethyl]methane; octadecyl-3-[N,N-diethyl aminoxy]-propanoate; 3-[N,N-dibenzylaminoxy]propanoic acid potassium salt; and 1,6-hexamethylene bis[3-(N-allyl-N-dodecyl aminoxy)propanoate].

11. Other additives, for example, plasticizers, lubricants, emulsifiers, pigments, optical brighteners, flameproofing agents, anti-static agents, blowing agents and thiosynergists such as dilaurylthiodipropionate or distearylthiodipropionate.

Hindered phenolic antioxidants may also be present in the polymer composition. Use of diphosphaspiroundecanes of the present invention may result in enhanced polymer protection by reducing the formation of color resulting from the presence of the phenols. Such phenolic antioxidants include n-octadecyl 3,5-di-tert-butyl-4-hydroxyhydrocinnamate, neopentanetetrayl tetrakis-(3,5-di-tert-butyl-4-hydroxyl-hydrocinnamate), di-n-octadecyl 3,5-di-tert-butyl-4-hydroxybenzyl-phosphonate, 1,3,5-tris(3,5-di-tert-butyl-4-hydroxybenzyl)isocyanurate, thiodiethylene bis(3,5-di-tert-butyl-4-hydroxyhydrocinnamate). 1,3,5-trimethyl-2,4,6-tris(3,5-di-tert-butyl-4-hydroxybenzyl)benzene, 3,6-di-oxaoctamethylene bis(3-methyl-5-tert-butyl-4-hydroxyhydrocinnamate), 2,6-di-tert-butyl-p-cresol, 2,2'-ethylidene-bis(4,6-di-tert-butylphenol), 1,3,5-tris-(2,6-dimethyl-4-tert-butyl-3-hydroxybenzyl)isocyanurate. 1,1,3-tris-(2-methyl-4-hydroxy-5-tert-butylphenyl)butane, 1,3,5-tris-[2-(3,5-di-tert-butyl-4-hydroxyhydrocinnamoyloxy)-ethyl]-isocyanurate, 3,5-di-(3,5-di-tert-butyl-4-hydroxybenzyl)-mesitol, hexa-methylene bis(3,5-di-tert-butyl-4-hydroxyhydrocinnamate), 1-(3,5-di-tert-butyl-4-hydroxyanilino)-3,5-di(octylthio)-s-triazine, N,N'-hexamethylene-bis(3,5-di-tert-butyl-4-hydroxyhydro-cinnamamide), calcium bis(ethyl-3,5-di-tert-butyl-4-hydroxybenzylphosphonate), ethylene bis[3,3-di(3-tert-butyl-4-hydroxyphenyl)butyrate], octyl 3,5-di-tert-butyl-4-hydroxybenzylmercaptoacetate, bis(3,5-di-tert-butyl-4-hydroxyhydrocinnamoyl)hydrazide, and N,N'-bis-[2-(3,5-tert-butyl-4-hydroxyhydroxocinnamoyloxy)-ethyl]9 -oxamide, and preferably neopentanetetrayl tetrakis(3,5-di-tert-butyl-4-hydroxyhydrocinnamate), n-octadecyl 3,5-di-tert-butyl-4-hydroxyhydrocinnamate, 1,3,5-trimethyl-2,4,6-tris(3,5-di-tert-butyl-4-hydroxy-benzyl)benzene, 1,3,5-tris-(3,5-di-tert-butyl-4-hydroxybenzyl)isocyanurate, 2,6-di-tert-butyl-p-cresol or 2,2'-ethylidene-bis(4,6-di-tert-butylphenol).

Other additives, such as oxazapholidines, may additionally or alternatively be present.

Likewise, the instant compounds prevent color formation when hindered amine light stabilizers are present, such hindered amines including bis(1,2,2,6,6-pentamethyl-4-piperidyl)-2-n-butyl-2-(3,5-di-tert-butyl-4-hydroxy-benzyl)malonate; bis(2,2,6,6-tetramethyl-4-piperidyl) sebacate; dimethylsuccinate polymer with 4-hydroxy-2,2,6,6-tetramethyl-1-piperidinethanol; and polymer of 2,4-dichloro-6-octylamino-s-triazine with N'-(2,2,6,6-tetramethyl-4-piperidyl)hexamethylene diamine.

Consistent with the invention, the diphosphaspiroundecanes of the invention may be added to the polymer at any time prior to or during fabrication into articles, and may be combined with the polymer by any of a variety of means known in the art, such as by preblending or by being fed directly into fabrication equipment.

The present invention may further be understood by reference to the specific embodiments outlined below, which are provided herein to illustrate various aspects of the invention, either by demonstrating an aspect of the invention, such as polymer stabilization or hydrolysis resistance, or providing a basis for comparison.

SPECIFIC EMBODIMENTS

Acid number, when measured, was determined by one of the following methods. The Sodium Butoxide Method was used to determine acid number for all examples unless indicated otherwise.

POTASSIUM HYDROXIDE METHOD

Bromo thymol (0.1% in 1-butanol) indicator solution is added (4–6 drops) to 100 ml of 1-butanol in a 250 ml Erlenmeyer flask. The butanol is neutralized to a blue-green endpoint of pH7 with 0.02N methanolic KOH (1.32 gm KOH (ACS, 85%) in anhydrous reagent grade methanol and diluted to 1 liter and standardized against standard 0.1N HCl). The sample to be tested is weighed to the nearest 0.1 gm and added to the flask. When the sample is a solid the contents of the flask are warmed slightly to 176° F. (80° C.) before addition of the sample. The appropriate sample weight to be used is determined from the following table:

| Weight to be used | Estimated Acid Number |
| --- | --- |
| 20 gm | less than 0.1 |
| 5 gm | 0.1–2.0 |
| 1 gm | greater than 2.0 |

After addition of the sample the flask is swirled to dissolve the sample, and the contents of the flask are then immediately titrated with 0.02N KOH (described above) to a blue-green endpoint.

SODIUM BUTOXIDE METHOD

Bromothymol blue indicator (0.1%) is prepared as described above. A 2 gm sample of the material to be tested is weighed out in a 250 ml Erlenmeyer flask to the nearest 0.01 gm. Methylene chloride (75 ml) is added to another Erlenmeyer flask, followed by 4–6 drops of the bromothymol indicator solution, and the resulting solution is neutralized with 0.02N sodium butoxide (0.46 gm sodium metal dissolved in anhydrous butanol, diluted to 1 liter and standardized against 0.01N HCl) to a blue-green endpoint of pH-7. The neutralized methylene chloride solution is then added to the flask containing the sample and swirled to dissolve the sample. The resulting solution is immediately titrated with 0.02N sodium butoxide (prepared as indicated above) to a blue-green endpoint.

The acid number for either method is obtained from the following equation:

$$\text{Acid Number} \atop \text{(mg. reagent/gm sample)} = \frac{(M)(N)(56.1)}{S}$$

where:

M = ml. titrating reagent consumed in the titration
N = normality of the titrating reagent
S = weight (gms) of sample Example 1 illustrates the preparation of a diphosphaspiroundecane of the present invention, 3,9-bis(2,4,6-tri-t-butylphenoxy)-2,4,8,10-tetroxa-3,9-diphosphaspiro[5.5]undecane.

EXAMPLE 1

A suspension of 210.1 gms (800 mmols) of 2,4,6-tri-t-butylphenol, 105.9 gms (400 mmols) of 3,9-dichloro-2,4,8,10-tetroxa-3,9-diphosphaspiro[5.5]undecane and 118 mL (847 mmols) of triethylamine was dissolved in 200 mL of chlorobenzene and refluxed and mechanically stirred under a nitrogen atmosphere for 46 hrs. The resulting dark brown suspension was diluted with 500 mL of chlorobenzene and filtered to remove triethylamine hydrochloride formed during the reaction. On cooling the filtrate, 214 gms of wet crystals were obtained. The crystals were recrystallized from toluene containing a small amount (less than 5 volume %) of triethylamine. The product was isolated by filtration to afford 76.2 g (26% yield) of bis(2,4,6-tri-t-butylphenoxy)-tetroxadiphosphaspiroundecane as crystals, with mp 253.5°–256° C. and acid number 3.0 (KOH-methanol method, described above). Further recrystallization from toluene containing a small amount of triethylamine afforded 48.8 g (17% yield) of the desired product as a white crystalline solid, mp 250°–255° C., acid number 0.99. Infrared, nmr, and mass spectroscopy confirmed the structure of the product.

Example 2 demonstrates preparation of bis(2,4,6-tri-t-butylphenoxy)-tetroxadiphosphaspiroundecane by a method preferred over the method of Example 1.

EXAMPLE 2

To a stirred solution of 120.3 g (458 mmol) of 2,4,6,-tri-t-butylphenol in 382 mL of tri-n-butylamine under argon was added 60.7 g (229 mmol) of 3,9-dichloro-2,4,8,10-tetroxa-3,9-diphosphaspiro[5.5]undecane. The suspension was then heated and stirred under argon at an internal temperature of 110° C. for 8 hrs. The resulting suspension was allowed to cool to room temperature and 400 mL of isopropyl alcohol added. Solids were isolated by vacuum filtration and washed on the funnel with an additional 1 L of isopropyl alcohol and then 1 L of n-heptane to afford 145.4 g (89% of theoretical yield) of the desired diphosphaspiroundecane as a white powder, with mp 253°–254° C. and acid number 0.92. This product was confirmed by standard methods.

Example 3 demonstrates preparation of bis(2,4,6-tri-t-butylphenoxy)-tetroxadiphosphaspiroundecane by another method preferred over the method of Example 1.

EXAMPLE 3

To 73.0 g (530 mmol) of phosphorus trichloride at approximately 0° C. was slowly added 16.9 g (170 mmol) of triethylamine. The mixture was stirred for ten minutes and then 35.0 g (130 mmol) of 2,4,6-tri-t-butylphenol was added in 7.0 g portions over a period of 20 minutes with continued cooling. After addition of 2,4,6-tri-t-butylphenol was complete the reaction mixture was heated at reflux for 3.5 hrs. and then allowed to cool to room temperature. The reaction mixture was diluted with 200 mL of heptane and cooled and filtered. The filter cake was washed twice with 80 mL (2×80) of heptane. Combined organic filtrates were concentrated under vacuum to afford 48.2 g (99% of theoretical yield) of the phosphorodichloridite as a solid product, with mp 81°–86° C. Similar results were obtained when this reaction was carried out in toluene solvent.

In the next step, a mixture of 47.0 g (130 mmol) of 2,4,6-tri-t-butylphenylphosphorodichloridite and 80 mL of toluene was added to 48.8 g (260 mmol) of pentaerythritol. An exotherm to 55° C. was accompanied by the formation of a white precipitate. After stirring for one hour the reaction mixture, which had returned to room temperature, was filtered under vacuum and the filter cake washed four times with 50 mL (4×50) of isopropyl alcohol. The resulting filter cake was dried to afford 33.2 g (71% of theoretical yield) of the desired diphosphaspiroundecane as a white solid, mp 253°–257° C., acid number 0.31. This product was confirmed by standard methods.

EXAMPLES 4–8

Other analogous spirocyclic compounds were synthesized by substituting other phenols for 2,4,6-tri-t-butylphenol in Example 1. These phenols were:

| Example | Phenol |
| --- | --- |
| 4 | 2,6-Di-t-butylphenol |
| 5 | 2,6-Di-t-butyl-4-methylphenol |
| 6 | 2,6-Di-t-butyl-4-ethylphenol |
| 7 | 2,6-Di-t-butyl-4-s-butylphenol |
| 8 | 2,4-Di-t-butylphenol |

Synthesis of the analogous diphosphaspiroundecanes was confirmed by one or more standard method, such as melting point, infrared spectroscopy (IR), nuclear magnetic resonance spectroscopy (NMR) and mass spectroscopy. The compounds thus prepared were used in the testing discussed in the following examples.

EXAMPLES 9–20

3,9-Bis(2,4-di-t-butyl-4-alkylphenoxy)-2,4,8-10-tetroxa-3,9-disphosphaspiro[5.5]undecanes as Stabilizers for LLDPE The stabilization effectiveness of variously substituted 3,9-bis(2,6-di-t-butyl-4-alkylphenoxy)-2,4,8,10-tetroxa-3,9-diphosphaspiro[5.5]undecanes during processing of Linear Low Density Polyethylene (LLDPE) was evaluated by incorporation of the spirodiphosphites into Unipol process resin GR-7042 available from the Union Carbide Corporation. Every test composition also included 500 ppm of calcium stearate as an acid neutralizer.

Powdered calcium stearate and diphosphaspiroundecane, or any other phosphite which was present, were incorporated into the GR-7042 powder by dry blending for 45 minutes in a Turbula blender. The dry blended resin mixture was extruded at a stock temperature of 525° C. through a one-inch single screw extruder equipped with a 2-stage screw fitted with a Maddox mixer. The extrudate was pelletized and reextruded for a total of seven extrusions. Material was saved from the first, third, fifth and seventh extrusions. The melt flow of these samples was measured using ASTM test method D-1238, Condition E.

The melt flow of LLDPE generally decreases with each extrusion as the polymer undergoes degradation by an overall crosslinking reaction, thereby decreasing melt flow. The efficiency of a stabilizer may therefore be evaluated by measuring its melt flow over successive extrusions and determining how close the melt flow of successive extrusions are to the melt flow of the initial extrusion.

The color of the retained samples was measured using a Hunter colormeter and standard techniques prescribed for use with that equipment, and comparing the yellowness index (YI) change between the first and seventh samples of each extrusion. The color measurements were made on one-eighth inch by one and one-half inch diameter discs that were compression molded at 330° F. from the retained sample pellets. Higher values indicate more color development.

For convenience, the diphosphaspiroundecane products of Examples 1, 4–8 were denoted as indicated below in Table I. (All are 3,9-bis(di or tri-alkylphenoxy)-2,4,8,10-tetroxa-3,9-diphosphaspiro[5.5]undecanes. However, all numbering except that of the alkyl substituents on the phenoxy moiety have been deleted below as a matter of convenience.)

Results of melt flow and color testing of LLDPE containing these compounds are indicated below in Table II. Loading levels of the diphosphaspiroundecanes in the LLDPE are indicated in parts per hundred parts resin. The headings "first, third, fifth, seventh" indicate the number of extrusions the composition had undergone when the sample was taken. "TBPP" denotes tris(2,4-di-t-butyl phenyl) phosphite, a noncyclic phosphite stabilizer known in the art.

EXAMPLES 21–27

3,9-Bis(2,6-di-t-butyl-4-alkylphenoxy)-2,4,8,10-tetroxa-3,9-diphosphaspiro[5.5]undecanes as Stabilizers for PP The 3,9-bis(2,6-di-t-butyl-4-alkylphenoxy)-2,4,8,10-tetroxa-3,9-diphosphaspiro[5.5]undecanes of Table I and of the present invention were evaluated in poly(propylene) as process stabilizers by comparing their performance in an unstabilized Ziegler-Natta process resin, Profax 6501 from Hercules. The resin powder was weighed together with 250 ppm of pentaerythritol tetrakis [3-(3,5-di-t-butyl-4-hydroxyphenyl)propionate], 500 ppm of calcium stearate, and 500 ppm of the phosphite. The resulting dry blend was mixed in a Turbula blender for 45 minutes. The dry blend was then extruded at a stock temperature of 525° F. to form polymer pellets. The pellets were reextruded under the same conditions for a total of five extrusions. Pellet samples saved from the first, third and fifth extrusions were measured for melt flow retention using ASTM D-1238, Condition L. Color measurements were made on one-eighth inch color discs compression molded from pellets retained from the first and fifth extrusions. Color measurements were done on a Hunter Colormeter. The yellowness index (YI) of the samples was used to compare the relative color of the specimens. The results of the testing appear in Table III.

EXAMPLES 28–34

Moisture Sensitivity of Substituted 3,9-Bis(2,6-di-t-butyl-4-alkyphenoxy)-2,4,8,10-tetroxa-3,9-diphosphaspiro[5.5]undecanes The moisture sensitivity of the spirocyclic diphosphites of Table I and of TBPP were examined by placing the compounds into an atmospheric chamber regulated at about 80% relative humidity. The samples were maintained in the chamber and monitored for weight gain and increase in acid value (AV) with respect to time. (Weight gain is an indication of the hygroscopic nature of the compound and may reflect sample hydrolysis, while an increase in acid value is indicative of some hydrolysis occuring in the sample.) The time required for the compounds to gain 1% weight during moisture exposure was assigned as the failure point. The results are indicated below in Table IV. Acid value was measured by the Na-butoxide/methylene chloride method both before the sample was placed in the atmospheric chamber (denoted "Initial AV") and after the sample had attained a 1% weight gain (denoted "Final AV").

EXAMPLES 35–41

Testing of Compound A, consistent with one embodiment of the invention, and TBPP and Compound E, not embodying the invention, were tested in GR7042 LLDPE containing 300 ppm of octadecyl 3,5-di-t-butyl-4-hydroxyhydrocinnamate, and 500 ppm of calcium stearate. Results of this testing are indicated below in Table V.

EXAMPLES 42–48

Additional testing was performed using Profax 6501 poly(propylene) resin. The compositions tested included 0.025 phr of pentaerythritol tetrakis [3-(3,5-di-t-butyl-4-hydroxy phenyl)propionate] and 0.05 phr. Ca Stearate. The amount of additive compound present and the results are indicated below in Table VI.

Data in Table V above indicate that 3,9-bis(2,4,6-tri-t-butylphenoxy)-2,4,8,10-tetroxa-3,9-diphosphaspiroundecane (Compound A) may exhibit greatly improved moisture resistance, as measured by weight gain, in comparison to other similar, analogous or homologous diphosphaspriounde canes, while data in Tables II, III, V and VI indicate that good polymer melt flow and color stabilization properties may be maintained.

The above examples are presented to illustrate various aspects of the invention. The invention is defined only by the following claims, and is not limited in scope to the particular embodiments or parameters described as modifications of these teachings will be apparent to those skilled in the art in view of the present disclosure.

TABLE I

| Compound | Example | Name |
| --- | --- | --- |
| A | 1 | bis(2,4,6-tri-t-butylphenoxy)-tetroxa-diphosphaspiroundecane |
| B | 4 | bis(2,6-di-t-butylphenoxy)-tetroxa-diphosphaspiroundecane |
| C | 5 | bis(2,6-di-t-butyl-4-methylphenoxy)-tetroxa-diphosphaspiroundecane |
| D | 6 | bis(2,6-di-t-butyl-4-ethylphenoxy)-tetroxa-diphosphaspiroundecane |
| E | 7 | bis(2,6-di-t-butyl-4-s-butylphenoxy)-tetroxa-diphosphaspiroundecane |
| F | 8 | bis(2,4-di-t-butylphenoxy)-tetroxa-diphòsphaspiroundecane |

TABLE II

| Example | Compound | Amount phr | Melt Flow, g/10 min first | third | fifth | seventh | Color, YI first | seventh |
|---|---|---|---|---|---|---|---|---|
| 9 | — | — | 1.63 | 1.02 | 0.78 | 0.62 | 11.24 | 18.84 |
| 10 | A | 0.04 | 2.11 | 1.73 | 1.23 | 0.98 | 9.87 | 15.07 |
| 11 | A | 0.07 | 2.18 | 2.12 | 1.90 | 1.40 | 10.40 | 14.58 |
| 12 | B | 0.04 | 2.10 | 1.60 | 1.13 | 0.91 | 9.78 | 14.69 |
| 13 | B | 0.07 | 2.16 | 2.07 | 1.78 | 1.47 | 15.25 | 13.90 |
| 14 | C | 0.04 | 2.13 | 1.88 | 1.32 | 0.98 | 10.35 | 13.70 |
| 15 | C | 0.07 | 2.20 | 2.10 | 2.08 | 1.65 | 10.05 | 14.05 |
| 16 | D | 0.04 | 2.08 | 1.61 | 1.07 | 0.86 | 9.72 | 15.69 |
| 17 | D | 0.07 | 2.15 | 2.09 | 1.62 | 1.20 | 9.85 | 15.35 |
| 18 | F | 0.04 | 2.13 | 1.89 | 1.47 | 1.21 | 10.10 | 14.47 |
| 19 | F | 0.07 | 2.20 | 2.16 | 2.01 | 1.67 | 9.39 | 12.73 |
| 20 | TBPP | 0.04 | 1.86 | 1.30 | 1.00 | 0.85 | 9.70 | 14.33 |

TABLE III

| Example | Compound | Amount phr | Melt Flow, g/10 min first | third | fifth | Color, YI first | fifth |
|---|---|---|---|---|---|---|---|
| 21 | — | — | 7.6 | 14.0 | 19.0 | 7.05 | 9.71 |
| 22 | A | 0.05 | 4.5 | 4.8 | 5.3 | 9.41 | 9.89 |
| 23 | B | 0.05 | 4.9 | 6.1 | 6.9 | 9.72 | 9.79 |
| 24 | C | 0.05 | 4.8 | 5.3 | 7.2 | 8.54 | 9.48 |
| 25 | D | 0.05 | 3.7 | 4.6 | 5.4 | 9.43 | 9.74 |
| 26 | F | 0.05 | 3.7 | 4.2 | 4.4 | 9.71 | 10.29 |
| 27 | TBPP | 0.05 | 5.0 | 6.7 | 9.9 | 10.15 | 10.42 |

TABLE IV

| Example | Compound | Time to 1% Weight Gain | Initial Av | Final AV |
|---|---|---|---|---|
| 28 | A | 1674 | 0.23 | 4.70 |
| 29 | B | 96 | 0.54 | 3.32 |
| 30 | C | 66 | 0.26 | 21.60 |
| 31 | D | 72 | 2.55 | 9.5 |
| 32 | E | 216 | 0.13 | 7 |
| 33 | F | 66 | 1.06 | 14.2 |
| 34 | TBPP | >1200 | 0.21 | 0.96 |

TABLE V

| Example | Compound | Amount phr | Melt Flow, g/10 min first | third | fifth | Color, YI first | fifth |
|---|---|---|---|---|---|---|---|
| 35 | — | — | 1.59 | 0.98 | 0.75 | 15.13 | 19.55 |
| 36 | A | 0.04 | 2.04 | 1.27 | 0.93 | 12.63 | 14.90 |
| 37 | A | 0.07 | 1.98 | 1.87 | 1.62 | 11.90 | 13.39 |
| 38 | E | 0.04 | 1.98 | 1.53 | 0.93 | 12.59 | 15.63 |
| 39 | E | 0.07 | 1.94 | 1.88 | 1.71 | 11.28 | 12.66 |
| 40 | TBPP | 0.04 | 1.64 | 1.19 | 0.86 | 13.44 | 18.57 |
| 41 | TBPP | 0.07 | 1.62 | 1.12 | 0.86 | 12.93 | 17.96 |

TABLE VI

| Example | Compound | Amount phr | Melt Flow, g/10 min first | third | fifth | Color, YI first | fifth |
|---|---|---|---|---|---|---|---|
| 42 | — | — | 5.7 | 12.4 | 19.4 | 8.9 | 9.78 |
| 43* | A | 0.05 | 2.1 | 2.6 | 3.2 | 9.39 | 9.56 |
| 44* | A | 0.0375 | 2.4 | 2.7 | 3.4 | 9.75 | 9.63 |
| 45 | E | 0.05 | 2.6 | 2.8 | 2.9 | 8.98 | 9.26 |
| 46 | E | 0.0375 | 2.0 | 3.0 | 4.2 | 8.04 | 9.47 |
| 47 | TBPP | 0.05 | 3.3 | 5.2 | 8.3 | 9.08 | 9.24 |
| 48 | TBPP | 0.0375 | 2.9 | 4.8 | 7.3 | 9.56 | 9.57 |

TABLE VII

| Example | Compound | Amount phr | Melt Flow, g/10 min first | third | fifth | Color, YI first | fifth |
|---|---|---|---|---|---|---|---|
| 43 | A | 0.05 | 2.0 | 2.7 | 3.4 | 9.06 | 9.16 |
|  |  |  | 2.6 | 2.8 | 3.3 | 9.37 | 9.50 |
|  |  |  | 2.1 | 2.6 | 3.2 | 9.39 | 9.56 |
|  |  |  | 2.1 | 2.3 | 2.7 | 9.25 | 9.56 |

TABLE VII-continued

| Example | Compound | Amount phr | Melt Flow, g/10 min first | third | fifth | Color, YI first | fifth |
|---|---|---|---|---|---|---|---|
| 44 | A | .0375 | 2.1 | 2.4 | 3.4 | 9.78 | 10.38 |
|  |  |  | 2.4 | 2.7 | 3.4 | 9.75 | 9.63 |
|  |  |  | 2.6 | 2.8 | 3.0 | 9.94 | 9.58 |
|  |  |  | 2.8 | 2.9 | 3.2 | 9.37 | 9.83 |

We claim:

1. A composition particularly useful for improving the melt flow stability and/or the color stability of polymers comprising a diphosphaspiroundecane of the general formula:

$$R^1 \text{—} \bigcirc \begin{smallmatrix} R^2 \\ \\ R^3 \end{smallmatrix} \text{—} O\text{—}P \begin{smallmatrix} O\text{—}CH_2 \\ \\ O\text{—}CH_2 \end{smallmatrix} C \begin{smallmatrix} CH_2\text{—}O \\ \\ CH_2\text{—}O \end{smallmatrix} P\text{—}O\text{—} \bigcirc \begin{smallmatrix} R^4 \\ \\ R^6 \end{smallmatrix} \text{—}R^5$$

wherein each of $R^1$, $R^2$, $R^3$, $R^4$, $R^5$ and $R^6$, is a tertiary-alkyl moiety.

2. The composition of claim 1 wherein $R^1$, $R^2$, $R^3$, $R^4$, $R^5$ and $R^6$ are independently selected from the group consisting of $C_4$ to about $C_{12}$ tertiary-alkyl moieties.

3. The composition of claim 2 wherein $R^1$, $R^2$, $R^3$, $R^4$, $R^5$, and $R^6$ are independently selected from the group consisting of t-butyl, t-pentyl, 1,1,4,4-tetramethyl butyl, t-dodecyl and 1-methylcyclohexyl moieties.

4. The composition of claim 3 wherein $R^1$, $R^2$, $R^3$, $R^4$, $R^5$, and $R^6$ are t-butyl moieties.

5. The composition of claim 1 wherein $R^1$, $R^2$, $R^3$, $R^4$, $R^5$, and $R^6$ are selected to be the same tertiary-alkyl moiety.

6. A polymer composition comprising a polymer and a sufficient amount of the diphosphaspiroundecane of claim 1 to improve the melt flow stability and/or the color stability of the polymer.

7. The composition of claim 6 wherein the polymer is selected from the group consisting of polyamide, polyolefin, polyester, polyphenylene ether, polycarbonate, polyvinylchlorides and styrenic resins, and mixtures thereof.

8. The composition of claim 7 wherein the polymer is selected from the group consisting of polyethylene, polyamide 6, polyamide 6/6, 6/10, 6/9, 6/12 and 4/6, polypropylene, polyethylene terephthalate, polybutylene terephthalate, polycarbonate, polyphenylene ether, polystyrene, polyvinylchloride, impact polystyrene, and ABS-type graft copolymer resins, and mixtures thereof.

9. The composition of claim 6 wherein said diphosphaspiroundecane compound is present in an amount equal to about 0.01 to about 2 phr.

10. The composition of claim 6 wherein said diphosphaspiroundecane is present in an amount equal to about 0.01 to about 1 phr.

* * * * *